(12) United States Patent
Otsubo et al.

(10) Patent No.: US 9,265,254 B2
(45) Date of Patent: Feb. 23, 2016

(54) GRANULAR PESTICIDAL COMPOSITION

(75) Inventors: Toshiro Otsubo, Sanda (JP); Rei Matsunaga, Kobe (JP); Eriko Takeko, Ashiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1262 days.

(21) Appl. No.: 11/256,002

(22) Filed: Oct. 24, 2005

(65) Prior Publication Data

US 2006/0089315 A1    Apr. 27, 2006

(30) Foreign Application Priority Data

Oct. 27, 2004 (JP) .................. 2004-311935
Feb. 14, 2005 (JP) .................. 2005-035812

(51) Int. Cl.
*A61K 31/4152* (2006.01)
*C07D 231/52* (2006.01)
*A01N 43/56* (2006.01)

(52) U.S. Cl.
CPC ...................... *A01N 43/56* (2013.01)

(58) Field of Classification Search
CPC ........................ A01N 43/56; A01N 2300/00
USPC ........................ 514/405; 548/368.7
See application file for complete search history.

(56) References Cited

U.S. PATENT DOCUMENTS

| | | | |
|---|---|---|---|
| 5,180,420 A | | 1/1993 | Katayama et al. |
| 5,200,401 A | * | 4/1993 | Rochling et al. ............. 514/63 |
| 5,354,742 A | * | 10/1994 | Deming et al. ............. 514/117 |
| 6,030,924 A | * | 2/2000 | Mayer et al. ............. 504/134 |
| 6,103,667 A | * | 8/2000 | Brunner et al. ............. 504/282 |
| 6,294,567 B1 | * | 9/2001 | Hashizume et al. ......... 514/404 |
| 6,521,568 B1 | * | 2/2003 | Kimura ............. 504/130 |
| 2003/0032559 A1 | | 2/2003 | Ziemer et al. |
| 2003/0148887 A1 | | 8/2003 | Bratz et al. |

FOREIGN PATENT DOCUMENTS

| | | | |
|---|---|---|---|
| JP | H11-049604 A | | 2/1999 |
| JP | 2000-204001 A | | 7/2000 |
| JP | 2002-179506 A | | 6/2002 |
| JP | 2002-316902 A | | 10/2002 |
| JP | 2002316902 A | * | 10/2002 |
| JP | 2004-043322 A | | 2/2004 |
| JP | 2004043322 A | * | 2/2004 |

OTHER PUBLICATIONS

English translation of the Brazilian Office Action for corresponding Brazilian Application No. PI0505775-2 issued Nov. 10, 2013 (received Jan. 8, 2014).
Japanese Office Action for Japanese Application No. 2005-302686, dated Jul. 12, 2011, with English language translation.

* cited by examiner

*Primary Examiner* — Janet Epps-Smith
*Assistant Examiner* — Courtney Brown
(74) *Attorney, Agent, or Firm* — Birch, Stewart, Kolasch & Birch, LLP

(57) ABSTRACT

A granular pesticidal composition which comprises a pyrazolinone compound given by the formula (1):

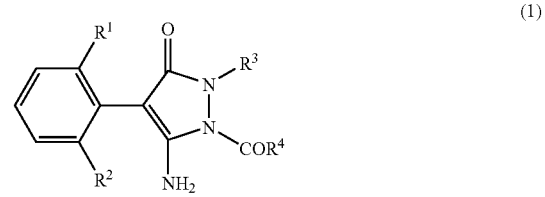

(1)

wherein $R^1$ represents a chlorine atom etc.; $R^2$ represents a chlorine atom etc.; $R^3$ represents a 1-methylethyl group etc.; and $R^4$ represents a C1-C4 alkoxy group etc.
and a salt of ligninsulfonic acid,
and the amount of the salt of ligninsulfonic acid in the granular pesticidal composition is 10-60% by weight
has good disintegrability in water when it is diluted with water.

12 Claims, No Drawings

GRANULAR PESTICIDAL COMPOSITION

FIELD OF THE INVENTION

The present invention relates to a granular pesticidal composition, particularly, a granular pesticidal composition having good disintegrability in water when it is diluted with water.

BACKGROUND ARTS

It is known that the pyrazolinone compounds given by the formula (1):

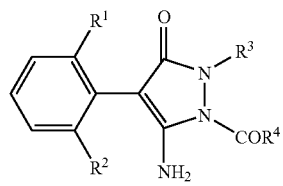

wherein $R^1$ represents a hydrogen atom, chlorine atom or methyl group; $R^2$ represents a chlorine atom or methyl group; $R^3$ represents a 1-methylethyl, 1,1-dimethylethyl, 1-methylpropyl, 1-ethylpropyl or 1-methylbutyl group; and $R^4$ represents a C1-C4 alkoxy, C3-C4 alkenyloxy, C3-C4 alkynyloxy, C1-C4 alkylthio, C3-C4 alkenylthio or C3-C4 alkynylthio group;
are useful as an active ingredient of an agent for controlling plant diseases.

The pyrazolinone compounds given by the formula (1) are known in U.S. Pat. No. 6,294,567, and some granular pesticidal compositions containing the pyrazolinone compounds are known in U.S. Pat. Nos. 6,294,567, 6,521,568 and JP-2002-316902A.

DISCLOSURE OF THE INVENTION

However, these granular compositions have poor disintegrability in water and it is difficult to give an aqueous dilution quickly. Thus, these granular compositions can be used for applying to soil and the like as they are; however, they are not suitable for spraying the dilution prepared by diluting them with water.

The present invention directs to a granular pesticidal composition, which contains the pyrazolinone compound given by the formula (1) as an active ingredient, having good disintegrability in water, in other words, a granular pesticidal composition that gives an aqueous dilution by quick disintegration in water when it is diluted with water.

According to the present invention, a granular pesticidal composition which comprises a pyrazolinone compound given by the formula (1):

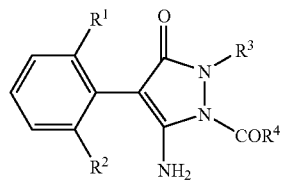

wherein $R^1$ represents a hydrogen atom, chlorine atom or methyl group; $R^2$ represents a chlorine atom or methyl group; $R^3$ represents a 1-methylethyl, 1,1-dimethylethyl, 1-methylpropyl, 1-ethylpropyl or 1-methylbutyl group; and $R^4$ represents a C1-C4 alkoxy, C3-C4 alkenyloxy, C3-C4 alkynyloxy, C1-C4 alkylthio, C3-C4 alkenylthio or C3-C4 alkynylthio group;
and a salt of ligninsulfonic acid,
and the amount of the salt of ligninsulfonic acid in the granular pesticidal composition is 10-60% by weight, preferably 20-50% by weight,
has good disintegrability in water.

The granular pesticidal composition of the invention is good at disintegrability in water when it is diluted with water.

The granular pesticidal composition of the invention is characterized by containing the pyrazolinone compound given by the formula (1) and a salt of ligninsulfonic acid, and that the amount of the salt of ligninsulfonic acid in the granular pesticidal composition is 10-60% by weight.

The pyrazolinone compounds given by the formula (1) contained in the granular pesticidal composition are known compounds in U.S. Pat. No. 6,294,567, and they can be prepared by the methods described therein.

In the pyrazolinone compounds given by the formula (1), examples of the C1-C4 alkoxy group for $R^4$ include methoxy, ethoxy, propoxy and butoxy group; examples of the C3-C4 alkenyloxy group include 2-propenyloxy and 3-butenyloxy group; C3-C4 alkynyloxy group include 2-propynyloxy, 2-butynyloxy and 3-butynyloxy group; examples of the C1-C4 alkylthio group include methylthio, ethylthio, propylthio and butylthio group; C3-C4 alkenylthio group include 2-propenylthio and 3-butenylthio group; and C3-C4 alkynylthio group include 2-propynylthio, 2-butynylthio and 3-butynylthio group.

Typical examples of the pyrazolinone compounds given by the formula (1) include 1-(methoxycarbonyl)-2-(1-methylethyl)-4-(2,6-dichlorophenyl)-5-amino-1H-pyrazol-3-one, 1-[(2-propenyloxy)carbonyl]-2-(1-methylethyl)-4-(2,6-dichlorophenyl)-5-amino-1H-pyrazol-3-one, 1-(ethoxycarbonyl)-2-(1-methylethyl)-4-(2,6-dichlorophenyl)-5-amino-1H-pyrazol-3-one, 1-[(2-propynyloxy)carbonyl]-2-(1-methylethyl)-4-(2,6-dichlorophenyl)-5-amino-1H-pyrazol-3-one, 1-[(3-butenyloxy)carbonyl]-2-(1-methylethyl)-4-(2,6-dichlorophenyl)-5-amino-1H-pyrazol-3-one, 1-[(2-butynyloxy)carbonyl]-2-(1-methylethyl)-4-(2,6-dichlorophenyl)-5-amino-1H-pyrazol-3-one, 1-[(3-butynyloxy)carbonyl]-2-(1-methylethyl)-4-(2,6-dichlorophenyl)-5-amino-1H-pyrazol-3-one, 1-[(ethylthio)carbonyl]-2-(1-methylethyl)-4-(2,6-dichlorophenyl)-5-amino-1H-pyrazol-3-one, 1-[(2-propenylthio)carbonyl]-2-(1-methylethyl)-4-(2,6-dichlorophenyl)-5-amino-1H-pyrazol-3-one, 1-[(2-propenyloxy)carbonyl]-2-(1-methylpropyl)-4-(2-methylphenyl)-5-amino-1H-pyrazol-3-one, 1-[(ethylthio)carbonyl]-2-(1-methylpropyl)-4-(2-methylphenyl)-5-amino-1H-pyrazol-3-one, 1-[(2-propenylthio)carbonyl]-2-(1-methylpropyl)-4-(2-methylphenyl)-5-amino-1H-pyrazol-3-one, 1-[(2-propynyloxy)carbonyl]-2-(1-methylpropyl)-4-(2,6-dichlorophenyl)-5-amino-1H-pyrazol-3-one, 1-[(3-butenyloxy)carbonyl]-2-(1-methylpropyl)-4-(2,6-dichlorophenyl)-5-amino-1H-pyrazol-3-one, 1-[(ethylthio)carbonyl]-2-(1-methylethyl)-4-(2-methylphenyl)-5-amino-1H-pyrazol-3-one, 1-[(2-propenylthio)carbonyl]-2-(1-methylethyl)-4-(2-methylphenyl)-5-amino-1H-pyrazol-3-one, 1-[(methylthio)carbonyl]-2-(1-methylethyl)-4-(2-methylphenyl)-5-amino-1H-pyrazol-3-one, 1-[(ethylthio)carbonyl]-2-(1-methylpropyl)-4-(2,6-dichlorophenyl)-5- amino-1H-pyrazol-3-one, 1-(ethoxycarbonyl)-2-(1-methylpropyl)-4-(2-methylphenyl)-5-amino-1H-pyrazol-3-one, 1-[(methylthio)carbonyl]-2-(1-methylethyl)-4-(2,6-dichlorophenyl)-5-amino-1H-pyrazol-3-one, 1-[(methylthio)carbonyl]-2-(1-methylpropyl)-4-(2,6-dichlorophenyl)-5-amino-1H-pyrazol-3-one, 1-[(2-propenylthio)carbonyl]-2-(1-methylpropyl)-4-(2-chlorophenyl)-5-amino-1H-pyrazol-3-one and 1-[(methylthio)carbonyl]-2-(1-methylpropyl)-4-(2-methylphenyl)-5-amino-1H-pyrazol-3-one.

The content of the pyrazolinone compounds given by the formula (1) in the granular pesticidal composition of the invention is usually 2-60% by weight, preferably 20-60% by weight, more preferably 40-60% by weight.

Ligninsulfonic acid, which is also called as lignosulfonic acid, is a lignin derivative and it can be produced by treating a material including lignin (e.g. wood) with sulfite, hydrosulfite or sulfurous acid.

The salts of ligninsulfonic acid are alkali metal salts, alkaline earth metal salts or ammonium salts in general.

Examples of the salt of ligninsulfonic acid include sodium ligninsulfonate, calcium ligninsulfonate and ammonium ligninsulfonate. In the present invention, the salt of ligninsulfonic acid on the market can be used as it is. Examples of the salt of ligninsulfonic acid are Reax 85A (sodium ligninsulfonate, commercial name of Westvaco Corp.), Reax 83A (sodium ligninsulfonate, commercial name of Westvaco Corp.), Reax 81A (sodium ligninsulfonate, commercial name of Westvaco Corp.), Ployfon H (sodium ligninsulfonate, commercial name of Westvaco Corp.), Ployfon O (sodium ligninsulfonate, commercial name of Westvaco Corp.), Ployfon T (sodium ligninsulfonate, commercial name of Westvaco Corp.), Ployfon F (sodium ligninsulfonate, commercial name of Westvaco Corp.), PC-876A (ammonium ligninsulfonate, commercial name of Westvaco Corp.), SANX P201 (calcium ligninsulfonate, commercial name of Nippon Paper Chemicals Co.), SANX P200 (calcium ligninsulfonate, commercial name of Nippon Paper Chemicals Co.), SANX P252 (sodium ligninsulfonate, commercial name of Nippon Paper Chemicals Co.), Kraftsperse EDF-350 (kraft sodium ligninsulfonate, commercial name of Westvaco Corp.) and Kraftsperse EDF-450 (kraft sodium ligninsulfonate, commercial name of Westvaco Corp.).

The content of the salt of ligninsulfonic acid in the granular pesticidal composition of the invention is usually 10-60% by weight, preferably 20-50% by weight.

The granular pesticidal composition of the invention may consist of the pyrazolinone compound given by the formula (1) and the salt of ligninsulfonic acid. And it can further contain a dispersant, carrier, an auxiliary (e.g., antifoaming agent, coloring agent) and so on, if required.

Examples of the dispersant include salts of alkylbenzenesulfonic acid, salts of polycarboxylic acid and salts of sulfuric ester.

Examples of the alkyl group in the salts of alkylbenzenesulfonic acid include C8-20 alkyl group. Examples of the salt in the salts of alkylbenzenesulfonic acid include sodium salt and calcium salt.

The salt of alkylbenzenesulfonic acid on the market can be used as it is for the present invention. Examples of the salt of alkylbenzenesulfonic acid on the market include Witconate 90Flakes (sodium salt of C10-13 alkylbenzenesulfonic acid, commercial name of Witco Corp.).

The salt of polycarboxylic acid on the market can be used as it is for the present invention. Examples of the salt of polycarboxylic acid on the market include Geropon SC/213 (potassium salt of carboxylic copolymer, commercial name of Rhodia Corp.).

Examples of the salt of sulfuric ester include sodium salt, potassium salt and calcium salt of higher (C10-20) alcohol sulfate. Typical example is sodium laurylsulfate.

The salt of sulfuric ester on the market can be used as it is for the present invention. Examples of the salt of sulfuric ester on the market include Emal 10 Powder (sodium laurylsulfate, commercial name of Kao Corp.).

When the granular pesticidal composition of the invention contains a dispersant, the content of the dispersant is usually 2-20% by weight, preferably 4-10% by weight.

The existence of the dispersant provides a good uniformity of the pyrazolinone compound given by the formula (1) in the aqueous dilution obtained by mixing the granular pesticidal composition of the invention with water; therefore, the addition of the dispersant is preferable.

The carrier may be a mineral carrier or water-soluble carrier. Examples of the mineral carrier include kaolin clay, diatomaceous earth, agalmatolite, silica, bentonite, terra alba, activated clay, attapalgite clay, pyrophyllite, sericite, zeolite, zeeklite, wollastonite, calcium silicate, calcium carbonate, talc, pumice and precipitated silica. Examples of the water-soluble carrier include ammonium salts such as ammonium sulfate and ammonium chloride; phosphates such as dipotassium hydrogen phosphate and potassium dihydrogen phosphate; carbonates such as sodium carbonate and sodium hydrogen carbonate; sugars such as glucose, fructose, sucrose, lactose and dextrin; urea; sodium chloride; sodium sulfate and polyethylene glycol being solid at room temperature. When the granular pesticidal composition of the invention contains a carrier, the carrier may be left on the leaves of crop as a stain after spraying an aqueous dilution of the granular pesticidal composition of the invention to the crop. To avoid the stain, the above-mentioned water-soluble carriers are preferably used.

When the granular pesticidal composition of the invention contains a carrier, the content of the carrier is generally 30% by weight or less, preferably 20% by weight or less. The amount of the carrier in the granular pesticidal composition of the invention is usually 5-30% by weight.

Examples of the embodiment of the granular pesticidal composition of the invention include the followings:

[1] A granular pesticidal composition which comprises a pyrazolinone compound given by the formula (1):

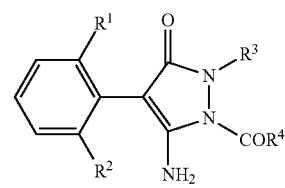

(1)

wherein $R^1$ represents a hydrogen atom, chlorine atom or methyl group; $R^2$ represents a chlorine atom or methyl group; $R^3$ represents a 1-methylethyl, 1,1-dimethylethyl, 1-methylpropyl, 1-ethylpropyl or 1-methylbutyl group; and $R^4$ represents a C1-C4 alkoxy, C3-C4 alkenyloxy, C3-C4 alkynyloxy, C1-C4 alkylthio, C3-C4 alkenylthio or C3-C4 alkynylthio group;

and a salt of ligninsulfonic acid, and the amount of the salt of ligninsulfonic acid in the granular pesticidal composition is 10-60% by weight, preferably 20-50% by weight.

[2] The granular pesticidal composition described in [1], wherein the pyrazolinone compound given by the formula (1) is 1-[(2-propenylthio) carbonyl]-2-(1-methylethyl)-4-(2-methylphenyl)-5-amino-1H-pyrazol-3-one.

[3] The granular pesticidal composition described in [1] or [2], which comprises the pyrazolinone compound given by the formula (1), a salt of ligninsulfonic acid and a dispersant, and the amount of the salt of ligninsulfonic acid in the granular pesticidal composition is 10-60% by weight, preferably 20-50% by weight.

[4] The granular pesticidal composition described in [3], which comprises 20-60% by weight, preferably 40-60% by weight of the pyrazolinone compound given by the formula (1), 10-60% by weight, preferably 20-50% by weight of a salt of ligninsulfonic acid and 2-20% by weight, preferably 4-10% by weight of a dispersant.

[5] The granular pesticidal composition described in [4], wherein the dispersant is a salt of alkylbenzenesulfonic acid, polycarboxylic acid or a salt of sulfuric ester.

[6] The granular pesticidal composition described in [4], wherein the dispersant is sodium laurylsulfate.

[7] The granular pesticidal composition described in [1] or [2], which comprises the pyrazolinone compound given by the formula (1), a salt of ligninsulfonic acid, a dispersant and a carrier, and the amount of the salt of ligninsulfonic acid in the granular pesticidal composition is 10-60% by weight, preferably 20-50% by weight.

[8] The granular pesticidal composition described in [1] or [2], which comprises 20-60% by weight, preferably 40-60% by weight of the pyrazolinone compound given by the formula (1), 10-60% by weight, preferably 20-50% by weight of a salt of ligninsulfonic acid, 2-20% by weight, preferably 4-10% by weight of a dispersant and 5-30% by weight of a carrier.

[9] The granular pesticidal composition described in [8], wherein the carrier is a water-soluble carrier.

[10] The granular pesticidal composition described in [1] or [2], which consists essentially of 20-60% by weight, preferably 40-60% by weight of the pyrazolinone compound given by the formula (1), 10-60% by weight, preferably 20-50% by weight of a salt of ligninsulfonic acid, 2-20% by weight, preferably 4-10% by weight of a dispersant and 5-30% by weight of a carrier.

The granular pesticidal composition of the invention can be, for example, produced by the methods of the following I to IV.

I. A method of spraying and drying an aqueous suspension containing a pyrazolinone compound given by the formula (1), a salt of ligninsulfonic acid and water, and optionally a dispersant and a carrier.

In this method, the aqueous suspension for spray-drying can be prepared by the method 1) or 2) below.

1) Adding a pyrazolinone compound given by the formula (1) and optionally a dispersant and/or a carrier to an aqueous solution of a salt of ligninsulfonic acid having a designated concentration, and wet-pulverizing with wet bead mill such as dyno-mill or wet pulverizing machine such as sand grinder.

2) Mixing a salt of ligninsulfonic acid and a pyrazolinone compound given by the formula (1) and optionally a dispersant and/or a carrier uniformly with a mixer such as ribbon mixer, juice mixer and nauta mixer, and then dry-pulverizing with a pulverizer such as hammer mill, pin mill, air mill and centrifugal pulverizer. If necessary, further mixing with a mixer, and then making the pulverized mixture suspended in a designated amount of water (optionally containing a dispersant) with a stirrer such as disperser.

In the wet-pulverizing or dry-pulverizing for preparing the aqueous suspension above, the crystals of the pyrazolinone compound given by the formula (1) are pulverized to make their particle diameter 1-15 µm, preferably 3-10 µm.

Spray-drying is carried out by making the aqueous suspension sprayed through a pressure spray-nozzle or rotary atomizer contact with hot wind. In the spray-drying, the particle diameter of the obtained granular pesticidal composition can be controlled by adjusting spraying amount (spraying rate) of the aqueous suspension through a pressure spray-nozzle or rotary atomizer, spray-drying temperature, amount of the provided hot wind, direction of the hot wind and so on. The condition is usually 80° C. or less of the nozzle temperature and 70° C. or less of the temperature of the granular pesticidal composition immediately after drying. In the present invention, the spray-drying condition is usually adjusted for making the particle diameter of the granular pesticidal composition 0.1-1 mm.

Further, the method of the invention includes a method of granulating the first particles sprayed and dried in part in a fluidized bed, namely a method of spraying an aqueous suspension containing a pyrazolinone compound given by the formula (1), a salt of ligninsulfonic acid and water, and optionally a dispersant and a carrier into the fluidized bed and making fluidized granulation after spray-granulation successively (Fluidized Spray Dry, FSD method).

In the method, the aqueous suspension sprayed into the fluidized bed can be prepared, for example, by the method of 1) or 2) described above.

In the wet-pulverizing or dry-pulverizing for preparing the aqueous suspension, the pulverization is carried out to make the particle diameter of the crystals of the pyrazolinone compound given by the formula (1) 1-15 µm, preferably 3-10 µm.

The obtained aqueous suspension is sprayed into the fluidized bed, for example, through a pressure spray-nozzle or rotary atomizer. When the sprayed mist contacts with hot wind in the fluidized bed and is dried, it agglomerates and forms a larger granular composition than the first particles immediately after spraying. The first particle diameter and the second one after agglomeration can be controlled by the condition of spraying amount (spraying rate) of the aqueous suspension through the pressure spray-nozzle or rotary atomizer, drying temperature in the fluidized bed, amount of the provided hot wind, direction of the hot wind and so on. The condition is usually adjusted for 30-70° C. of the temperature of the granular composition immediately after drying. In the present invention, the condition is usually adjusted for making the particle diameter (second particle diameter) of the granular pesticidal composition 0.5-3 mm.

II. A method of adding water to a mixture of a pyrazolinone compound given by the formula (1), a salt of ligninsulfonic acid, and optionally a dispersant and a carrier; kneading; and granulating by extruding the kneaded product.

In this method, the pulverized mixture of a pyrazolinone compound given by the formula (1), a salt of ligninsulfonic acid, and optionally a dispersant and a carrier is usually used. The pulverization can be carried out, for example, with dry-pulverizer such as jet mill, pin mill and hammer mill. The pulverization is usually carried out to make ultimately the particle diameter of the crystals of the pyrazolinone compound given by the formula (1) 1-15 µm, preferably 3-10 m.

A designated amount of water is added to the mixture, which is kneaded and granulated by extruding the kneaded product. The extrusion is usually carried out with a screen having 0.5-2.0 mmφ, preferably 0.6-11.0 mmφ in the hole.

After the extrusion, the product is dried usually at 30-70° C., preferably 30-60° C. to give the granular pesticidal composition of the invention.

III. A method of granulating a powdery mixture of a pyrazolinone compound given by the formula (1), a salt of ligninsulfonic acid, and optionally a dispersant and a carrier in a fluidized bed.

The powdery mixture containing a pyrazolinone compound given by the formula (1), a salt of ligninsulfonic acid, and optionally a dispersant and/or a carrier is obtained by dry-pulverizing a mixture of the pyrazolinone compound given by the formula (1), the salt of ligninsulfonic acid, and optionally the dispersant and/or the carrier with a dry-pulverizer such as jet mill, pin mill and hammer mill. The pulverization is usually carried out to make ultimately the particle diameter of the crystals of the pyrazolinone compound given by the formula (1) 1-15 μm, preferably 3-10 μm.

The fluidized granulation is carried out by making the powdery mixture fluidity in a fluidized device such as jet stream fluidized bed type and jet stream type, and spraying water (optionally containing a salt of ligninsulfonic acid and/or dispersant) thereto.

In the granulation in the fluidized bed, the particle diameter of the obtained granular pesticidal composition can be controlled by adjusting the conditions at the granulation such as fluidity and diameter of sprayed droplet. The temperature of the granules in the fluidized bed is usually in the range of 30-70° C. In the present invention, the granulation conditions in the fluidized bed are adjusted for making the particle diameter of the obtained granular pesticidal composition 0.5-5.0 mm in general.

IV. A method of tumbling granulation of a powdery mixture of a pyrazolinone compound given by the formula (1), a salt of ligninsulfonic acid, and optionally a dispersant and a carrier.

The powdery mixture containing a pyrazolinone compound given by the formula (1), a salt of ligninsulfonic acid, and optionally a dispersant and/or a carrier is obtained by dry-pulverizing a mixture of the pyrazolinone compound given by the formula (1), the salt of ligninsulfonic acid, and optionally the dispersant and/or the carrier with a dry-pulverizer such as jet mill, pin mill and hammer mill. The pulverization is usually carried out to make ultimately the particle diameter of the crystals of the pyrazolinone compound given by the formula (1) 1-15 μm, preferably 3-10 μm.

The tumbling granulation is carried out by making the powdery mixture tumble with an action of agitation paddle in a container such as pan, dram and vibration type, and then spraying water (optionally containing a salt of ligninsulfonic acid and/or dispersant) thereto to accelerate the growth of the granules.

In the tumbling granulation, the particle diameter of the obtained granular pesticidal composition can be controlled by adjusting the conditions at the granulation such as amount of water, rate of adding water, position of adding water, rotary rate of the container and rate of adding the powdery mixture. The temperature of the tumbling granulation is usually in the range of 30-70° C. In the present invention, the tumbling granulation conditions are adjusted for making the particle diameter of the obtained granular pesticidal composition 0.3-3 mm in general.

In the present invention, the weight of the granular composition which is basis of each component of the granular pesticidal composition does not contain residual water after granulation-drying or increased humidity by moisture absorption during preservation.

The granular pesticidal composition of the invention generally has a size of 0.1-5 mm in diameter. It can be used as granule, but it is usually used as water dispersible granules; thus it is used by diluted with water and applied to crops in general.

When the granular pesticidal composition of the invention is diluted with water, 25 to 5000 parts by weight of water is used for one part by weight of the granular pesticidal composition of the invention in general.

When the aqueous dilution of the granular pesticidal composition of the invention is applied to crops, the application amount is 0.01-50 g, preferably 0.05-10 g at the amount of the pyrazolinone compound given by the formula (1) per 100 m$^2$.

The granular pesticidal composition of the invention can be used for controlling various plant diseases such as *Pyricularia oryzae*, *Cochliobolus miyaheanus* and *Rhizoctonia solani* of rice; *Erysiphe graminis*, f sp. *hordei*, f. sp. *tritici*, *Gibherella zeae*, *Puccinia striiformis*, *P. graminis*, *P. recondite*, *P. hordei*, *Typhula* sp., *Micronectriella nivalis*, *Ustilago tritici*, *U. nuda*, *Tilletia caries*, *Pseudocercosporella herportrichoides*, *Rhizoctonia cerealis*, *Rhynchosporium secalis*, *Septoria tritici* and *Leptosphaeria nodorum* of wheat and barley; *Diaporthe citri* and *Elsinoe fawcetti* of citrus; *Penicillium digitatum* and *P. itanicum* of fruits; *Sclerotinia mali*, *Valsa mali*, *Podosphaera leucotricha*, *Alternaria mali* and *Venturai inaequalis* of apple; *Venturia nasshicola*, *Alternaria kikuchiana* and *Gymnosporangium haraeanum* of pear; *Sclerotinia cinerea*, *Cladosporium carpophilum* and *Phomopsis* sp. of peach; *Plasmopara viticola*, *Elsinoe ampelina*, *Glomerella cingulata*, *Uncinula necator* and *Phakopora ampelopsidis* of grape; *Gloeosporium kaki*, *Cercospora kaki* and *Mycospharerella nawae* of persimmon; *Pseudoperonospora cubensis* of cucumber; *Colletotrichum lagenarium*, *Sphaerotheca fuliginea* and *Mycosphaerella melonis* of gourds; *Alternaria solani*, *Cladosporium fulvum* and *Phytophthora infestans* of tomato; *Phomopsis vexans* and *Erysiphe cichoracearum* of eggplant; *Alternaria japonica* and *Cercosporella brassicae* of Cruciferae vegetables; *Puccinia allii* of leek; *Cercospora kikuchii*, *Elsinoe glycines* and *Diaporthe phaseolorum* var. *sajae* of soybean; *Colletotrichum lindemthianum* of kidney bean; *Mycosphaerella personatum* and *Cercospora arachidicola* of peanut; *Erysiphe pisi* and *Peronospora pisi* of pea; *Peronospora viciae* and *Phytophthora nicotianae* of broad bean; *Alternaria solani* and *Phytophthora infestans* of potato; *Sphaerotheca humuli* and *Phytophthora nicotianae* of strawberry; *Exohasidium recticulatum* and *Erysiphe leucospila* of tea; *Alternaria longipes*, *Erysiphe cichoracearum*, *Colletotrichum tabacum* and *Phytophthora parasitica* of tobacco; *Cercospora heticola* of sugar beet; *Diplocarpon rosae*, *Sphaerotheca pannosa* and *Phytophthora megasperma* of rose; *Septoria chrysanthemiindici* and *Puccinia horiana* of chrysanthemum; and *Botrytis cinerea*, *Sclerotinia sclerotiorum* and *Pythium* sp. of various crops, especially, effective for controlling plant diseases by *Botrytis cinerea*, *Sclerotinia sclerotiorum* and *Sclerotinia cinerea*.

In the granular pesticidal composition of the invention, the weight ratio of the pyrazolinone compound given by the formula (1) and the salt of ligninsulfonic acid is preferably in the rage of 1:0.4 to 1:4. When the granular pesticidal composition of the invention is used for controlling the above-mentioned plant diseases, it is expected that the efficacy will increase.

EXAMPLES

Hereinafter, the present invention is explained more concretely; however, the invention is not restricted by the following examples.

Production Example 1

A mixture, obtained by mixing 42 parts by weight of 1-[(2-propenylthio)carbonyl]-2-(1-methylethyl)-4-(2-methylphenyl)-5-amino-1H-pyrazol-3-one, 20 parts by weight of sodium ligninsulfonate (Reax 85A produced by Westvaco Corp.), 5 parts by weight of sodium alkylbenzenesulfonate (Witconate 90 Flakes produced by Witco Corp.), 5 parts by weight of potassium polycarbonate (Geropon SC/213 produced by Rhodia Corp.), 10 parts by weight of ammonium sulfate and 18 parts by weight of kaolin clay (Shokozan A clay produced by Shokozan Company), was dry-pulverized with an air mill. The particle diameter of 1-[(2-propenylthio)carbonyl]-2-(1-methylethyl)-4-(2-methylphenyl)-5-amino-1H-pyrazol-3-one crystals after pulverizing was 5.2 µm.

Twenty (20) parts by weight of water were added to the pulverized product, kneaded, extruded through 0.7 mmϕ screen and dried (with hot air at 60° C. for 10 minutes) to give a granular pesticidal composition of the invention.

Production Example 2

Into a stainless beaker, 114 parts by weight of deionized water and 278 parts by weight of glass beads (1.0-1.5 mmϕ) were added and stirred. Thirty-four (34) parts by weight of sodium ligninsulfonate (Reax 85A produced by Westvaco Corp.), 5 parts by weight of potassium polycarbonate (Geropon SC/213 produced by Rhodia Corp.) and 10 parts by weight of dipotassium hydrogen phosphate were added thereto, and further 51 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 µm).

Sprayed amount: 9 ml of slurry per minute
Spray-dried temperature: 110° C. at entrance and 65-70° C. at exit (product temperature)
Direction of heat wind: the upper to lower of spray tower

Production Example 3

A mixture, obtained by mixing 21 parts by weight of 1-[(2-propenylthio)carbonyl]-2-(1-methylethyl)-4-(2-methylphenyl)-5-amino-1H-pyrazol-3-one, 10 parts by weight of calcium ligninsulfonate (SANX P201 produced by Nippon Paper Chemicals Company), 4 parts by weight of sodium lauryl sulfate (Emal 10 Powder produced by Kao Corp.) and 65 parts by weight of kaolin clay (Shokozan A clay produced by Shokozan Company), was dry-pulverized with a centrifugal pulverizer. The particle diameter of 1-[(2-propenylthio)carbonyl]-2-(1-methylethyl)-4-(2-methylphenyl)-5-amino-1H-pyrazol-3-one crystals after pulverizing was 6.4 µm.

Twenty (20) parts by weight of water were added to the pulverized product, kneaded, extruded through 0.7 mmϕ screen and dried (with hot air at 60° C. for 15 minutes) to give a granular pesticidal composition of the invention.

Production Example 4

Into a stainless beaker, 114 parts by weight of deionized water and 278 parts by weight of glass beads (1.0-1.5 mmϕ) were added and stirred. Forty-three (43) parts by weight of sodium ligninsulfonate (Reax 85A produced by Westvaco Corp.), 5 parts by weight of potassium polycarbonate (Geropon SC/213 produced by Rhodia Corp.) and 10 parts by weight of ammonium sulfate were added thereto, and further 42 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 µm).

Sprayed amount: 9 ml of slurry per minute
Spray-dried temperature: 110° C. at entrance and 65-70° C. at exit (product temperature)
Direction of heat wind: the upper to lower of spray tower

Production Example 5

Into a stainless beaker, 114 parts by weight of deionized water and 278 parts by weight of glass beads (1.0-1.5 mmϕ) were added and stirred. Thirty-two (32) parts by weight of sodium ligninsulfonate (Reax 85A produced by Westvaco Corp.), 5 parts by weight of potassium polycarbonate (Geropon SC/213 produced by Rhodia Corp.) and 10 parts by weight of ammonium sulfate were added thereto, and further 53 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 µm).

Sprayed amount: 9 ml of slurry per minute
Spray-dried temperature: 110° C. at entrance and 65-70° C. at exit (product temperature)
Direction of heat wind: the upper to lower of spray tower

Production Example 6

Into a stainless beaker, 114 parts by weight of deionized water and 278 parts by weight of glass beads (1.0-1.5 mmϕ) were added and stirred. Thirty-four (34) parts by weight of sodium ligninsulfonate (Reax 85A produced by Westvaco Corp.), 5 parts by weight of potassium polycarbonate (Geropon SC/213 produced by Rhodia Corp.) and 10 parts by weight of potassium dihydrogen phosphate were added thereto, and further 50 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 µm).

Sprayed amount: 9 ml of slurry per minute
Spray-dried temperature: 110° C. at entrance and 65-70° C. at exit (product temperature)
Direction of heat wind: the upper to lower of spray tower

Production Example 7

Into a stainless beaker, 114 parts by weight of deionized water and 278 parts by weight of glass beads (1.0-1.5 mmϕ) were added and stirred. Forty-five (45) parts by weight of sodium ligninsulfonate (Reax 85A produced by Westvaco Corp.), 5 parts by weight of potassium polycarbonate (Geropon SC/213 produced by Rhodia Corp.) were added thereto, and further 50 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 μm).
Sprayed amount: 9 ml of slurry per minute
Spray-dried temperature: 110° C. at entrance and 65-70° C. at exit (product temperature)
Direction of heat wind: the upper to lower of spray tower Production Example 8

Into a stainless beaker, 114 parts by weight of deionized water and 278 parts by weight of glass beads (1.0-1.5 mmϕ) were added and stirred. Thirty-four and nine-tenths (34.9) parts by weight of sodium ligninsulfonate (Reax 85A produced by Westvaco Corp.), 5 parts by weight of potassium polycarbonate (Geropon SC/213 produced by Rhodia Corp.) and 10 parts by weight of potassium dihydrogen phosphate and 0.1 parts by weight of antifoaming agent (Antifoam C produced by Dowcoaning Agia Corp.) were added thereto, and further 50 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 μm).
Sprayed amount: 9 ml of slurry per minute
Spray-dried temperature: 110° C. at entrance and 65-70° C. at exit (product temperature)
Direction of heat wind: the upper to lower of spray tower Production Example 9

Into a stainless beaker, 114 parts by weight of deionized water and 278 parts by weight of glass beads (1.0-1.5 mmϕ) were added and stirred. Thirty-four and nine-tenths (34.9) parts by weight of sodium ligninsulfonate (Reax 85A produced by Westvaco Corp.), 5 parts by weight of potassium polycarbonate (Geropon SC/213 produced by Rhodia Corp.) and 10 parts by weight of dipotassium hydrogen phosphate and 0.1 parts by weight of antifoaming agent (Antifoam C produced by Dowcoaning Agia Corp.) were added thereto, and further 50 parts by weight of 1-[(2-propenylthio)carbonyl]-2-(1-methylethyl)-4-(2-methylphenyl)-5-amino-1H-pyrazol-3-one were added and continued to stir for 40 minutes for wet-pulverizing. The glass beads were filtered off with nylon net to give a slurry, which was spray-dried with a spray-drier (SD-1 type produced by Tokyo Rikakiki Company) to give a granular pesticidal composition of the invention (average particle diameter: about 50 μm).
Sprayed amount: 9 ml of slurry per minute
Spray-dried temperature: 110° C. at entrance and 65-70° C. at exit (product temperature)
Direction of heat wind: the upper to lower of spray tower Production Example 10

A mixture, obtained by mixing 2 parts by weight of 1-[(2-propenylthio)carbonyl]-2-(1-methylethyl)-4-(2-methylphenyl)-5-amino-1H-pyrazol-3-one, 1 part by weight of synthetic hydrated silica (Tokuseal GU-N produced by Tokuyama Corp.), 10 parts by weight of calcium ligninsulfonate (SANX P201H produced by Nippon Paper Chemicals Company), 30 parts by weight of bentonite (Bentonite Fuji produced by Hojun Corp.) and 57 parts by weight of kaolin clay (Shokozan A clay produced by Shokozan Company) in a polyethylene bag, was dry-pulverized with a centrifugal pulverizer.
About 24 parts by weight of water were added to the pulverized product, kneaded, extruded through 0.7 mmϕ screen and dried (with hot air at 60° C. for 10 minutes) to give a granular pesticidal composition of the invention.

Production Example 11

A mixture, obtained by mixing 2 parts by weight of 1-[(2-propenylthio)carbonyl]-2-(1-methylethyl)-4-(2-methylphenyl)-5-amino-1H-pyrazol-3-one, 1 part by weight of synthetic hydrated silica (Tokuseal GU-N produced by Tokuyama Corp.), 10 parts by weight of calcium ligninsulfonate (SANX P201H produced by Nippon Paper Chemicals Company), 22 parts by weight of bentonite (Bentonite Fuji produced by Hojun Corp.) and 65 parts by weight of kaolin clay (Shokozan A clay produced by Shokozan Company) in a polyethylene bag, was dry-pulverized with a centrifugal pulverizer.
About 24 parts by weight of water were added to the pulverized product, kneaded, extruded through 0.7 mmϕ screen and dried (with hot air at 60° C. for 10 minutes) to give a granular pesticidal composition of the invention.

Reference Production Example 1

A mixture, obtained by mixing 2 parts by weight of 1-[(2-propenylthio)carbonyl]-2-(1-methylethyl)-4-(2-methylphenyl)-5-amino-1H-pyrazol-3-one, 1 part by weight of synthetic hydrated silica (Tokuseal GU-N produced by Tokuyama Corp.), 2 parts by weight of sodium ligninsulfonate (Reax 85A produced by Westvaco Corp.), 30 parts by weight of bentonite (Bentonite Fuji produced by Hojun Corp.) and 65 parts by weight of kaolin clay (Shokozan A clay produced by Shokozan Company), was dry-pulverized with a centrifugal pulverizer.
Twenty (20) parts by weight of water were added to the pulverized product, kneaded, extruded through 0.7 mmϕ screen and dried (with hot air at 60° C. for 10 minutes) to give a granular pesticidal composition for comparison.

Reference Production Example 2

A mixture, obtained by mixing 2 parts by weight of 1-[(2-propenylthio)carbonyl]-2-(1-methylethyl)-4-(2-methylphenyl)-5-amino-1H-pyrazol-3-one, 1 part by weight of synthetic hydrated silica (Tokuseal GU-N produced by Tokuyama Corp.), 2 parts by weight of calcium ligninsulfonate (SANX P201H produced by Nippon Paper Chemicals Company), 30 parts by weight of bentonite (Bentonite Fuji produced by Hojun Corp.) and 65 parts by weight of kaolin clay (Shokozan A clay produced by Shokozan Company) in a polyethylene bag, was dry-pulverized with a centrifugal pulverizer.
About 24 parts by weight of water were added to the pulverized product, kneaded, extruded through 0.7 mmϕ screen and dried (with hot air at 60° C. for 10 minutes) to give a granular pesticidal composition for comparison.

Next, the disintegrability in water of the granular pesticidal composition of the invention is given by the test examples.

Test Example 1

A 50 ml-volume cylinder with a stopper containing 50 ml of hard water (CIPAC standard water D, 342 ppm of hardness) was set in a thermostat of 20° C. Each 500 mg of the granular pesticidal composition for the test was added to the cylinder, which was then turned upside down. This upside-down turning was repeated at a rate of once per two seconds. The number of the repetition of the upside-down turning was observed to complete disintegration of the granular pesticidal composition. The result is shown in Table 1.

TABLE 1

| Granular pesticidal composition provided for test | Number of repetition of upside-down turning for complete disintegration |
| --- | --- |
| Production example 1 | 11 |
| Production example 2 | 6 |
| Production example 3 | 11 |
| Production example 4 | 20 |
| Production example 5 | 19 |
| Production example 6 | 12 |
| Production example 7 | 10 |
| Production example 8 | 12 |
| Production example 9 | 8 |
| Reference production example 1 | 50 or more |

Test Example 2

A granular pesticidal composition (250 mg) for the test was added to a 250 ml-volume cylinder with a stopper containing 250 ml of hard water of 20° C. (CIPAC standard water D) and treated with ultrasonic wave for 2 minutes in a water tank with a ultrasonic apparatus. The cylinder was then turned upside down 30 times. After allowing it to stand for 15 minutes, 25 ml of the suspension were taken out from the center of the cylinder. The amount of 1-[(2-propenylthio)carbonyl]-2-(1-methylethyl)-4-(2-methylphenyl)-5-amino-1H-pyrazol-3-one (A) in the suspension was measured by quantitative analysis of liquid chromatography.

Separately, the amount of 1-[(2-propenylthio)carbonyl]-2-(1-methylethyl)-4-(2-methylphenyl)-5-amino-1H-pyrazol-3-one (B) in the granular pesticidal composition (250 mg) was calculated from the charged amount for the granular pesticidal composition. The following formula gave the degree of dispersion (%).

The degree of dispersion (%)=1000×(A/B)

The result is shown in Table 2.

TABLE 2

| Granular pesticidal composition provided for test | Degree of dispersion (%) |
| --- | --- |
| Production example 10 | 103 |
| Production example 11 | 100 |
| Reference production example 2 | 10 |

One hundred percents (100%) of the degree of dispersion given above mean that the granular pesticidal composition is disintegrated and dispersed uniformly in the dilution. The granular pesticidal compositions of Production examples 6 and 7 have good disintegrability in water, and the pyrazolinone compound given by the formula (1) in the granular pesticidal compositions is easily dispersed. On the other hand, the granular pesticidal composition of Reference production example 2, which is the formulation described in Formulation Example 4 of U.S. Pat. No. 6,294,567, has poor disintegrability in water. Thus, in Reference production example 2, the concentration of the pyrazolinone compound given by the formula (1) in the dilution is low and may be insufficient for controlling plant diseases when the formulation is used as water dispersible granule.

What is claimed is:

1. A granular pesticidal composition which comprises a pyrazolinone compound which is 1-[(2-propenylthio) carbonyl]-2-(1-methylethyl)-4-(2-methylphenyl)-5-amino-1H-pyrazol-3-one as a sole pesticidal active ingredient;
   and a salt of ligninsulfonic acid in which the salt is a sodium salt or a calcium salt, and
   the amount of the pyrazolinone compound in the granular pesticidal composition is 40-60% by weight, and the amount of the salt of ligninsulfonic acid in the granular pesticidal composition is 10-60% by weight.

2. The granular pesticidal composition according to claim 1, wherein the amount of the salt of ligninsulfonic acid in the granular pesticidal composition is 20-50% by weight.

3. The granular pesticidal composition according to claim 1, which comprises the pyrazolinone compound, the salt of ligninsulfonic acid and a dispersant, and the amount of the salt of ligninsulfonic acid in the granular pesticidal composition is 10-60% by weight.

4. The granular pesticidal composition according to claim 3, which comprises 40-60% by weight of the pyrazolinone compound, 10-60% by weight of the salt of ligninsulfonic acid and 2-20% by weight of a dispersant.

5. The granular pesticidal composition according to claim 4, wherein the dispersant is a salt of alkylbenzenesulfonic acid.

6. The granular pesticidal composition according to claim 4, wherein the dispersant is a salt of polycarboxylic acid.

7. The granular pesticidal composition according to claim 4, wherein the dispersant is a salt of sulfuric ester.

8. The granular pesticidal composition according to claim 7, wherein the salt of sulfuric ester is sodium laurylsulfate.

9. The granular pesticidal composition according to claim 1, which comprises the pyrazolinone compound, the salt of ligninsulfonic acid, a dispersant and a carrier, and the amount of the salt of ligninsulfonic acid in the granular pesticidal composition is 10-60% by weight.

10. The granular pesticidal composition according to claim 1, which comprises 40-60% by weight of the pyrazolinone compound, 10-60% by weight of the salt of ligninsulfonic acid, 2-20% by weight of a dispersant and 5-30% by weight of a carrier.

11. The granular pesticidal composition according to claim 10, wherein the carrier is a water-soluble carrier.

12. The granular pesticidal composition according to claim 1, which consists essentially of 40-60% by weight of the pyrazolinone compound, 10-60% by weight of the salt of ligninsulfonic acid, 2-20% by weight of a dispersant and 5-30% by weight of a carrier.

* * * * *